(12) United States Patent
Larkin (10) Patent No.: US 8,376,958 B2
(45) Date of Patent: Feb. 19, 2013

(54) GYNECOLOGICAL CONTAINER CAP HAVING A BOUNDARY CONFIGURED TO DETACH A GYNECOLOGICAL SAMPLER FROM A SAMPLING DEVICE

(76) Inventor: Daniel Larkin, St. Paul, MN (US)

( * ) Notice: Subject to any disclaimer, the term of this patent is extended or adjusted under 35 U.S.C. 154(b) by 397 days.

(21) Appl. No.: 12/274,180

(22) Filed: Nov. 19, 2008

(65) Prior Publication Data

US 2010/0124780 A1    May 20, 2010

(51) Int. Cl.
*A61B 10/00* (2006.01)
*C12M 1/26* (2006.01)
*C12M 3/00* (2006.01)
*B65D 51/16* (2006.01)
*B65D 41/00* (2006.01)

(52) U.S. Cl. ..... 600/569; 600/562; 600/570; 435/307.1; 435/309.1; 215/307; 215/310; 215/316; 215/354

(58) Field of Classification Search .................. 600/562, 600/569, 570, 572, 573; 435/309.1, 30, 307.1, 435/296, 292; 215/354, 226, 227, 200, 307, 215/310, 324; 222/478, 713, 570, 569, 540, 222/490, 499, 498; 604/317, 319
See application file for complete search history.

(56) References Cited

U.S. PATENT DOCUMENTS

| | | | |
|---|---|---|---|
| 4,803,998 | A | 2/1989 | Kezes et al. |
| 5,370,128 | A | 12/1994 | Wainwright |
| 5,422,273 | A | 6/1995 | Garrison et al. |
| 6,291,234 | B1 | 9/2001 | Raz et al. |
| 6,383,804 | B1 | 5/2002 | Ward, Jr. et al. |
| 6,394,966 | B1 | 5/2002 | Gill et al. |
| 6,521,190 | B1 | 2/2003 | Edens et al. |
| 7,413,551 | B2 | 8/2008 | Decker et al. |

*Primary Examiner* — Jeffrey G Hoekstra
*Assistant Examiner* — Megan Leedy
(74) *Attorney, Agent, or Firm* — Dicke, Billig & Czaja, PLLC (57) ABSTRACT

A cap for a container is described that is configured to retain a gynecological sample collected with a sampling device. The cap includes a peripheral wall extending between a base and a flange opposite the base, and a diaphragm extending from the base of the peripheral wall. The flange projects beyond the peripheral wall and is configured to seat against a rim of the container. The diaphragm defines a first open area communicating with a second open area that is smaller than the first open area and includes a boundary spaced from the peripheral wall that is configured to detach the distally located sampler from the sampling device.

15 Claims, 8 Drawing Sheets

GYNECOLOGICAL CONTAINER CAP HAVING A BOUNDARY CONFIGURED TO DETACH A GYNECOLOGICAL SAMPLER FROM A SAMPLING DEVICE

BACKGROUND

The Papanicolaou test ("Pap" test or "Pap smear") has proven to be valuable in the early detection of cervical precancerous and cancerous growths. The Pap test refers to the collection of cells from the cervical face, the endocervical canal, and occasionally from the vaginal wall.

The cells are collected with a sampling device. Suitable sampling devices include sampling brushes sold under the trademark Cervex-Brush® available from Rovers® medical and those described in U.S. patent application Ser. No. 11/588,120. The sampling devices are provided with a detachable swab that is removed from the sampling device after cell collection. For example, a physician or other clinician takes a cell sample from the patient with the swab, which is sent to a lab for analysis, and discards the remaining part of the sampling device.

After cell collection, the swab portion of the sampling device is deposited into a container holding preservation liquid. The collected cells are thus dispersed in the preservation liquid. One suitable container is provided in the SurePath™ liquid-based Pap test system available from Becton Dickinson of Franklin Lakes, N.J. The cells are preserved, and subsequently randomized, enriched with diagnostic material, pipetted, stained, and ultimately prepared (e.g., smeared) on a microscope slide for visualization of epithelial and other diagnostically relevant cells.

Depositing the swab into the container without splashing the cells/preservation liquid can be challenging. For example, conventional gynecological sampling jars include some form of a cover (e.g., a screw-on cover or the like) that fits on the container holding the preservation liquid. The cover is removed to access the preservation liquid, which can result in undesirable splashing/spilling of the liquid when introducing the swab portion to the container.

In particular, some sampling devices are designed to have the swab separated from a handle portion by snapping the swab off at a break line formed on the handle. Snapping the swab off is best accomplished using two hands, and is it possible to bump the container and spill the liquid when separating the swab from the handle. Other sampling devices are designed with a broom-style swab that slides off of a distal end of the handle portion. In any regard, depositing the swab into the container of preservation liquid can cause splashes, which undesirably has the potential to both diminish the volume of the collected sample and pose an infection risk to the healthcare worker.

Pap tests have proven to be useful in the early detection of malignant cells and are related to a reduction in the incidence and death rate due to cervical cancers. Improvements in the collection of cells during Pap tests will be welcomed by the medical community and patients alike.

SUMMARY

One embodiment provides a cap for a container configured to retain a gynecological sample collected with a sampling device having a distally located sampler coupled to a shaft. The cap includes a peripheral wall extending between a base and a flange opposite the base, and a diaphragm extending from the base of the peripheral wall. The flange projects beyond the peripheral wall and is configured to seat against a rim of the container. The diaphragm defines a first open area communicating with a second open area that is smaller than the first open area and includes a boundary spaced from the peripheral wall that is configured to detach the distally located sampler from the sampling device.

One embodiment provides a gynecological sampling system having a sampling device, a container configured to retain preservative liquid, and a cap configured to be inserted in a top opening of the container. The sampling device has a shaft and a cell sampler coupled to a distal end of the shaft. The cap includes a peripheral wall extending between a base and a flange opposite the base, and a diaphragm extending from the base of the peripheral wall. The flange projects beyond the peripheral wall and is configured to seat against a rim of the top opening of the container. The diaphragm defines a first open area communicating with a second open area. The diaphragm is configured to minimize splashing of the preservative liquid from the container and has a constriction between the first open area and the second open area that is configured to detach the cell sampler from the shaft of the sampling device.

BRIEF DESCRIPTION OF THE DRAWINGS

The accompanying drawings are included to provide a further understanding of embodiments and are incorporated in and constitute a part of this specification. The drawings illustrate embodiments and together with the description serve to explain principles of embodiments. Other embodiments and many of the intended advantages of embodiments will be readily appreciated as they become better understood by reference to the following detailed description. The elements of the drawings are not necessarily to scale relative to each other. Like reference numerals designate corresponding similar parts.

DETAILED DESCRIPTION

In the following Detailed Description, reference is made to the accompanying drawings, which form a part hereof, and in which is shown by way of illustration specific embodiments in which the invention may be practiced. In this regard, directional terminology, such as "top," "bottom," "front," "back," "leading," "trailing," etc., is used with reference to the orientation of the Figure(s) being described. Because components of embodiments can be positioned in a number of different orientations, the directional terminology is used for purposes of illustration and is in no way limiting. It is to be understood that other embodiments may be utilized and structural or logical changes may be made without departing from the scope of the present invention. The following detailed description, therefore, is not to be taken in a limiting sense, and the scope of the present invention is defined by the appended claims.

It is to be understood that the features of the various exemplary embodiments described herein, such as the closed cap area, may be combined with each other, unless specifically noted otherwise.

Embodiments provide a cap that is insertable into an uncovered gynecological sampling container. The cap is configured to minimize splashing of preservative liquid from the container as a portion of a sampling device is placed in the container.

Some sampling devices include a detachable sampling head extending from a shaft of the device. In one embodiment, the cap includes a converging channel that is configured to pry the sampling head from the sampler. Some sampling devices include a swab attached to a snap-apart shaft of the device. In one embodiment, the boundary comprises a fulcrum edge that is configured to apply a mechanical advantage to the shaft and break the swab off of the shaft.

Figure 1:
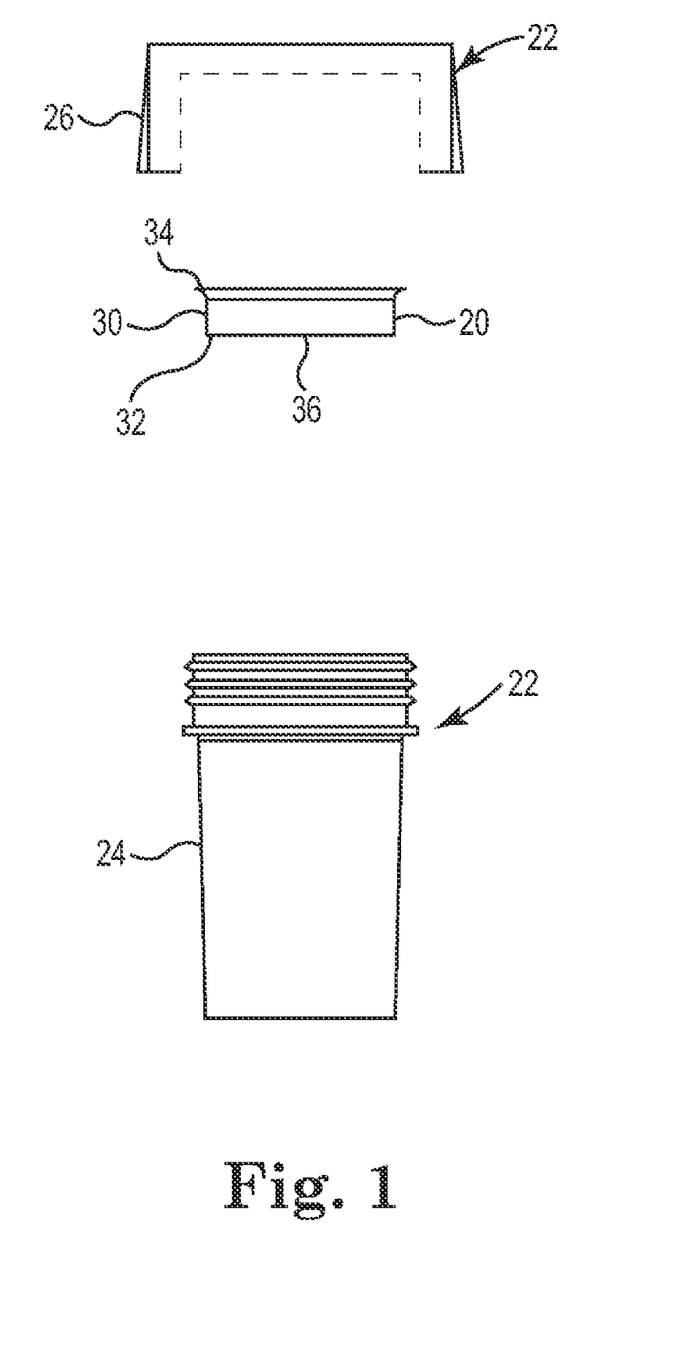
FIG. 1 is an exploded side view of a cap insertable into a gynecological sample preparation jar according to one embodiment.

FIG. 1 is an exploded side view of a cap 20 that is insertable into a gynecological sample preparation jar 22 according to one embodiment. The jar 22 includes a container 24 and a cover 26 that fits over the container 24 to retain preservative liquid (not shown) and receive cells collected in a Pap smear. The cap 20 is inserted in and seals to an inside diameter of the container 24 in a manner that minimizes splashing and spraying of liquid from the container 24.

The jar 22 is sized to hold several milliliters of preservative liquid and to receive a swab portion of a gynecological sampling device. Suitable jars include the SurePath™ liquid-based Pap test jar available from Becton Dickinson, Franklin Lakes, N.J.

Conventional jars for collecting gynecological samples are provided with a cover that is removed from the container to access the preservative liquid retained inside the container. The open container can undesirably spill or splash the preservative liquid and/or the collected Pap smear cell sample. Conventional Pap test jars have the potential to be cumbersome to use and are predisposed to splashing or spilling the preservative liquid due to the open top of the uncovered container.

Embodiments provide a cap 20 that is inserted into the container 24 to minimize or prevent splashing or spilling of the preservative liquid from the container 24. In addition, embodiments of the cap 20 provide a boundary or a channel or a fulcrum edge configured to assist in detaching a Pap test sampler from the sampling device.

In one embodiment, the cap 20 includes a peripheral wall 30 extending between a base 32 and a flange 34 that is opposite the base 32. The flange 34 projects outward from the peripheral wall 30 and is configured to seat against a rim of the container 24. A diaphragm 36 is provided extending from the base 32 of the peripheral wall 30. The diaphragm is thus located at a lower portion of the cap 20 and extends between the generally circular (in cross-section) peripheral wall 30.

Figure 2A:
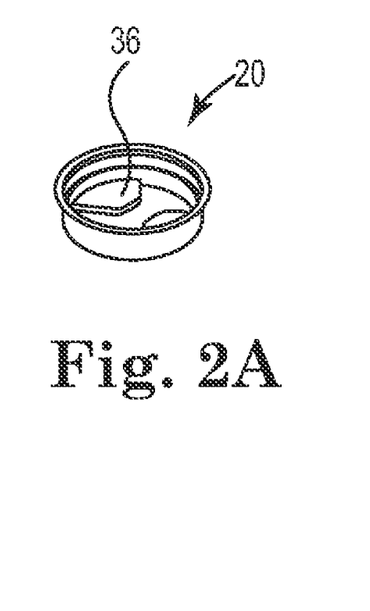
FIG. 2A is a perspective view and FIG. 2B is a top view of a cap insertable into the jar illustrated in FIG. 1 according to one embodiment.
Figure 2B:
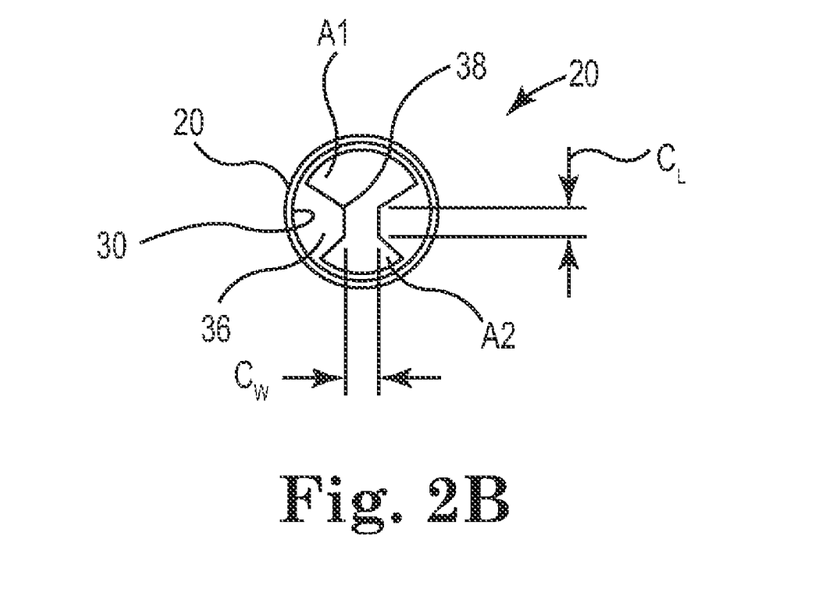

FIG. 2A is a perspective view and FIG. 2B is a top view of the cap 20 according to one embodiment. The diaphragm 36 extends between the peripheral wall 30 to provide an opening formed by area A1 and area A2 and a channel C (formed by a channel length Cl and a channel width Cw), and a closed area provided by the diaphragm 36. In one embodiment, the closed area of the diaphragm 36 is about equal to the open area provided by A1, A2, and C, such that when a sampling device is placed in the opening formed by the cover 20, the diaphragm 36 minimizes splashing out of the container. In one embodiment, the peripheral wall 30 defines or surrounds a total area of about 3.75 in$^2$, and the total open area (A1 and A2 and C) is about half of the total area and the closed diaphragm area is about half of the total area.

In general, the second open area A2 is smaller than the first open area A1. In one embodiment, the diaphragm 36 includes a boundary 38 that is spaced away from the peripheral wall 30 and is configured with an edge to be used for detaching a swab from a cell sampling device.

In one embodiment, the channel area C is disposed at an approximate middle of the diaphragm 36 such that the boundary 38 provides a central boundary. In one embodiment, the boundary 38 is formed by a combination of a perimeter of A1 and channel C. In one embodiment, the boundary 38 is formed by a perimeter of area A2 and the channel C. In one embodiment, the channel C is defined by a lateral dimension or width Cw that is narrower than a width of first open area A1 or a width of first open area A2. In this embodiment, the channel C forms a constriction (or necks down) between the first open area A1 and the second open area A2 to provide opposing spaced edges that are positioned to pry a cell sampler from a cell sampling device.

It is desirable for area A1 to large enough to receive a cell sampling swab from a sampling device (for example the open area A1 is sized to have a lateral dimension or a width of about 0.9 inches), and it is desirable to size the open area A2 to be smaller than the cross-sectional area of the cell sampling device. Hence, when the sampler is inserted into the larger open area A1 and trapped under the diaphragm 36 within area A2, the swab may be pried against the boundary 38 for removal from the sampling device handle.

In one embodiment, the boundary 38 provides a fulcrum edge that is configured to apply a mechanical advantage to the shaft. For example, when the swab is inserted into the cover 20, the boundary 38 functions as a fulcrum edge to apply a shear stress to the sampler shaft and snap the shaft apart, leaving the swab to drop into (or remain in) the container.

In one embodiment, the perimeter of the first open area A1 includes a base edge adjacent to the peripheral wall, where the base edge is the fulcrum edge.

Suitable dimensions for the lateral width of the channel Cw range between about 0.15-0.40 inches. Suitable lengths for the channel Cl range between about 0.10-0.30 inches, although other suitable dimensions are also acceptable.

Figure 3A:
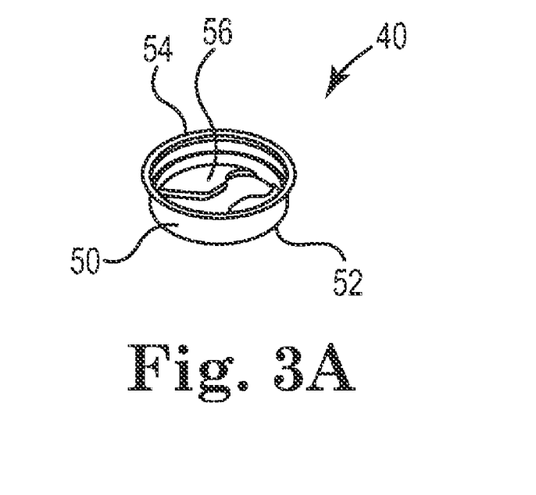
FIG. 3A is a perspective view and FIG. 3B is a top view of a cap insertable into the jar illustrated in FIG. 1 according to another embodiment.
Figure 3B:
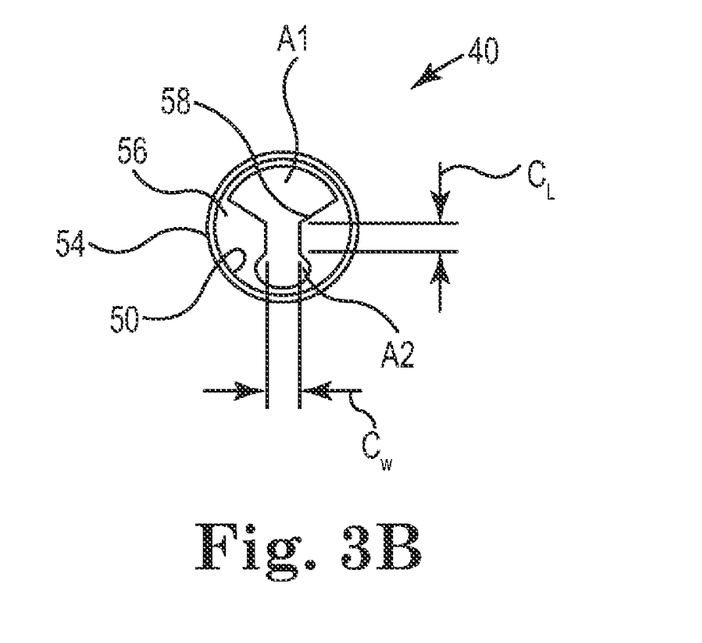

FIG. 3A is a perspective view and FIG. 3B is a top view of a cap 40 according to another embodiment. The cap 40 includes a peripheral wall 50 extending between a base 52 and a flange 54, and includes a diaphragm 56 extending from the base 52 of the peripheral wall 50.

In one embodiment, the diaphragm 58 is fabricated to provide a second area A2 that is smaller than a first area A1, where the areas A2, A1 communicate with each other through a channel C. In one embodiment, the diaphragm 56 provides a boundary 58 spaced from the peripheral wall 50. The boundary 58 is configured to engage with a cell sampler or a swab of a sampling device to facilitate separating the swab from a shaft of the sampling device. The channel C forms a constriction where the lateral dimension of the channel width Cw and length Cl are sized in ranges similar to those described above.

Area A1 is generally sized to receive the swab of the sampling device, and area A2 is generally sized to be smaller than the cross-sectional area of the swab. Capturing the swab under the diaphragm 56 enables detachment or separation of the swab from its handle.

Figure 4A:
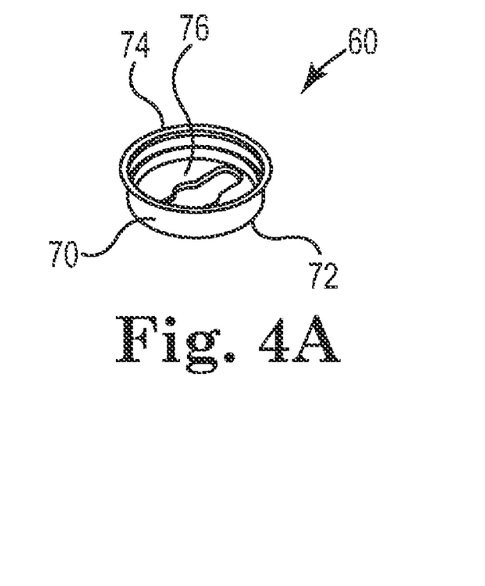
FIG. 4A is a perspective view and FIG. 4B is a top view of a cap insertable into the jar illustrated in FIG. 1 according to another embodiment.
Figure 4B:
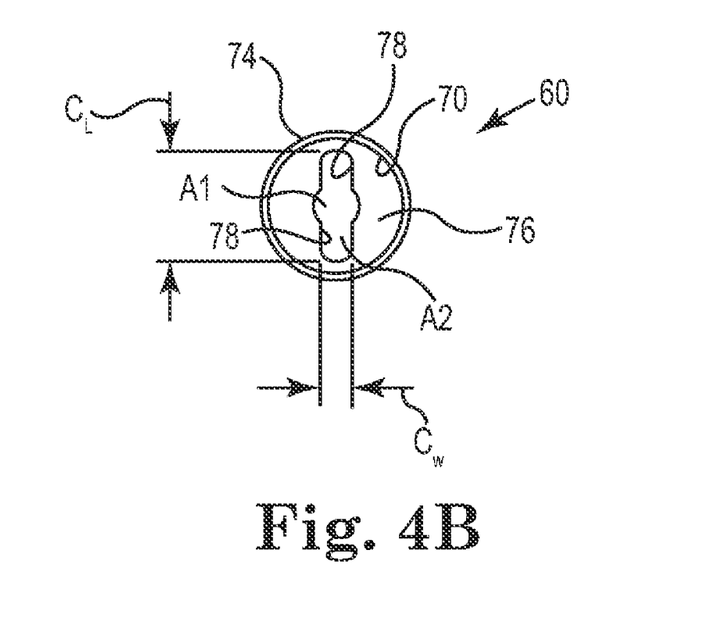

FIG. 4A is a perspective view and FIG. 4B is a top view of a cap 60 according to another embodiment. The cap 60 includes a peripheral wall 70 extending between a base 72 and a flange 74 and provides a diaphragm 76 extending from the base 72 of the peripheral wall 70. In one embodiment, a first open area A1 is provided that is larger than second open area A2, where area A1 is centrally located relative to the diaphragm 76. The diaphragm 76 provides a boundary 78 that is offset from the peripheral wall 70. The boundary 78 provides a fulcrum edge configured to impart a mechanical advantage in detaching a cell sampler from its shaft.

The diaphragm 76 provides a closed area configured to minimize splashing and spilling of preservative liquid from the jar 22 (FIG. 1). In general, area A2 is less than area A1 and the dimensions for the width of the channel Cw and the length of the channel Cl are similar to those described above. In one embodiment, the area of the closed surface of the diagram 76 is greater than the sum of the area A1, A2 and the channel C.

The boundary 78 converges in two locations where area A1 necks down to area the smaller area A2. During use, the swab is aligned with the openings and then rotated by about 180 degrees to engage with diaphragm 76. In this manner, the diaphragm 76 provides secure engagement with the swab, which is useful in detaching the swab from its shaft. The boundary 78 includes one or more corners defined by a perimeter edge of open areas A1, A2. In one embodiment, the perimeter edge of the boundary 78 provides a fulcrum edge that imparts a mechanical advantage when prying or severing a swab from a shaft of a sampling device.

Figure 5A:
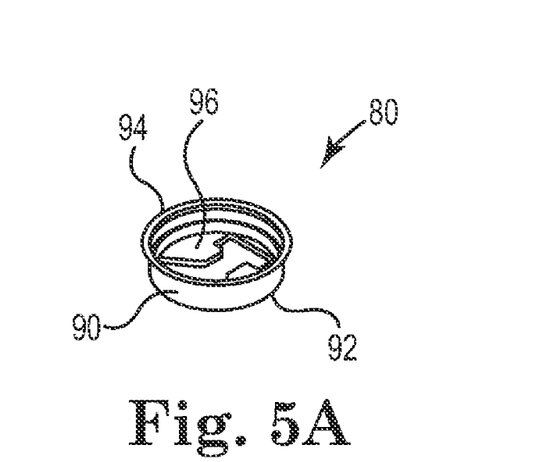
FIG. 5A is a perspective view and FIG. 5B is a top view of a cap insertable into the jar illustrated in FIG. 1 according to another embodiment.
Figure 5B:
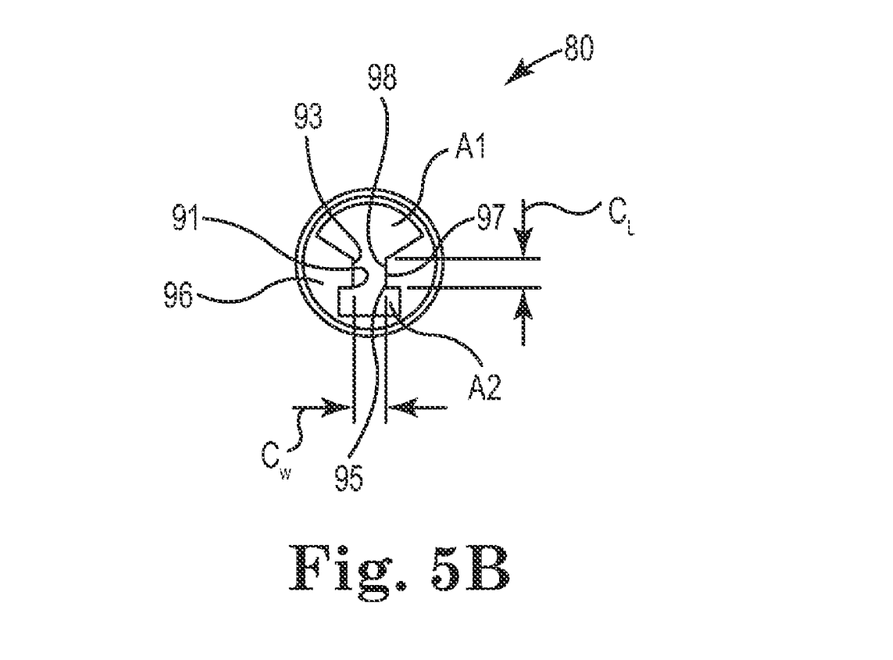

FIG. 5A is a perspective view and FIG. 5B is a top view of a cap 80 according to another embodiment. The cap 80 includes a peripheral wall 90 extending between a base 92 and a flange 94, where a diaphragm 96 is provided extending from the base 92 of the peripheral wall 90. Similar to the embodiments described above, the diaphragm 96 includes a boundary 98 that is employed to provide a mechanical advantage when detaching a swab from a sampling device. The diaphragm 96 includes a closed area and an open channel C extending between a first open area A1 and a second open area A2. Area A1 is generally greater than area A2 and converges toward area A2 through the channel C. The dimensions for the channel width Cw and the channel length Cl are similar to those provided above.

In one embodiment, the second open area A2 is approximately rectangular in shape and the boundary 98 includes a first corner 91 on a first side 93 of the channel area and a second corner 95 separated from the first corner 91 on an opposing second side 97 of the channel area. The first corner 91 intersects with a first channel edge of the channel area and the second corner 95 intersects with a second channel edge of the channel area. The corners 91, 95 are configured to engage with and separate the swab portion from its shaft. In one embodiment, the corners 91, 95 are right angle corners.

Figure 6:
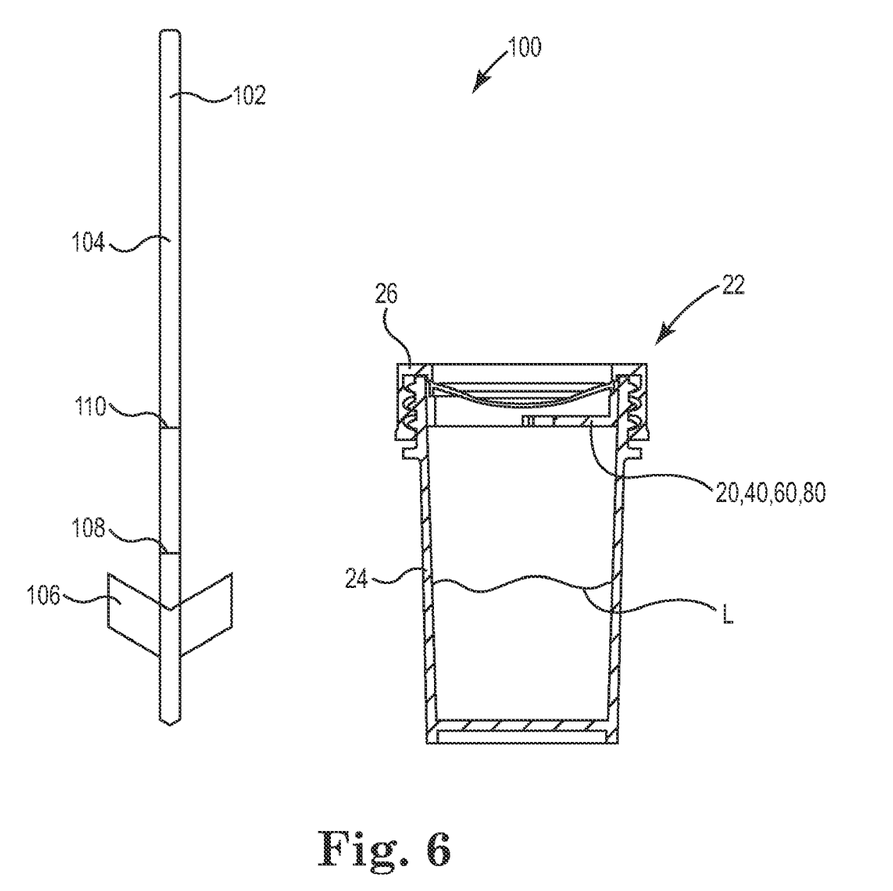
FIG. 6 is a schematic cross-sectional view of a gynecological sampling system including a sampling device and a cap inserted between a container and a cover of a jar according to one embodiment.

FIG. 6 is a schematic cross-sectional view of a gynecological sampling system 100 according to one embodiment. The gynecological sampling system 100 (system 100) includes the jar 22 with the container 24, the cover 26, any one of the caps 20, 40, 60, or 80 inserted into the container 24, and a sampling device 102. Suitable sampling devices include those described in U.S. patent application Ser. No. 11/588,120, the sampling brushes sold under the trademark Medscand CytoBrush Plus, spatula-styled samplers, or the sampling brush sold under the trademark Rovers® CervixBrush®.

In one embodiment, the sampling device 102 includes a shaft 104 and a cell sampler 106 coupled to a distal end of the shaft 104. In one embodiment, the cell sampler 106 is removable from the shaft 104 along a detach line 108. In one embodiment, the shaft 104 is provided with a break line 110 that is configured to enable the cell sampler 106 to be snapped off of the shaft 104.

The system 100 is illustrated as a kit in which one of the caps 20, 40, 60, 80 is inserted into the container 24. Preservation liquid L for preserving the cells collected by the sampler 106 is retained within the container 24. During use, a cell sample is swabbed from the patient with the sampler 106. The cover 26 is removed from the container 24 and the sampler 106 is deposited into the preservation liquid L. The cap 20 enables detachment of the sampler 106 from the shaft 104 and minimizes spilling and splashing of the cell sample and the liquid L.

The caps 20, 40, 60, 80 are fabricated from plastic and configured to seal along an inside diameter of the container 24. Suitable plastics for caps 20, 40, 60, 80 include polyethylene, polypropylene, silicone, or other suitable plastics.

Figure 7:
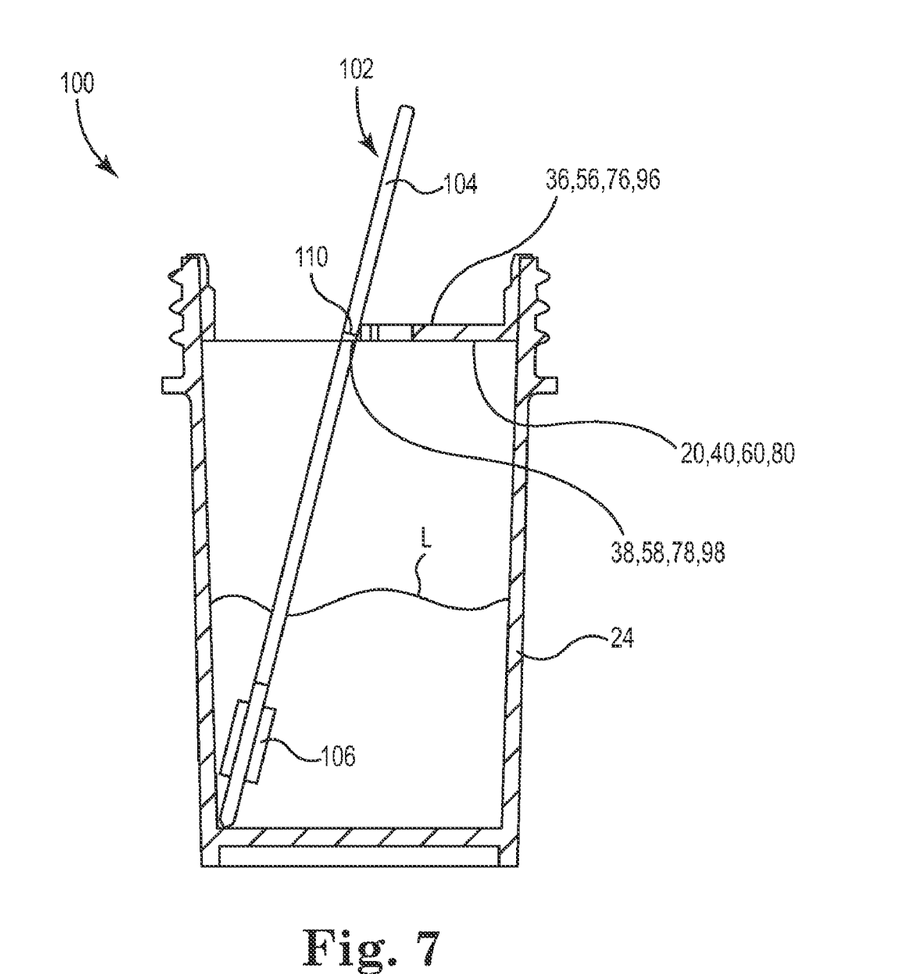
FIG. 7 is a schematic cross-sectional view of the container of FIG. 6 with the cover removed and the sampling device placed in the container.

FIG. 7 is a schematic cross-sectional view of the container 24 with the cover 26 (FIG. 6) removed. In general, the sampling device 102 is inserted through the larger area A1 and into the container 24 such that the cell sampler 106 is immersed in the preservation liquid L, after which the shaft 104 is moved into engagement with the smaller area A2 to position the cell sampler 106 for removal. For example, the cell sampler 106 is passed through the larger area A1, which is sized to provide clearance for insertion of the cell sampler 106 into the container 24. In one embodiment, the break line 110 is situated in contact with the boundary 38 (or the boundary 58, 78, 98). For example, and with reference to FIGS. 3B and 5B, the shaft 104 is moved from the larger area A1 into which the cell sampler 106 has been inserted and then moved into engagement with the smaller area A2. The sampling device 102 is wedged between the inside of the container 24 and the boundary 38 of A2, which provides a fulcrum edge for snapping the shaft 104 at the break line 110. In one embodiment, the shaft 104 is captured between two opposing fulcrum edges (FIGS. 3B and 5B, for example). In this regard, the shaft 104 is analogous to a lever and the fulcrum edge 38 is analogous to a fulcrum consistent with simple levers and Newton's laws. Subsequent lateral force applied to the shaft 104 snaps the shaft at the break line 110 (i.e., the shaft 104 is captured within area A2), thus depositing the cell sampler 106 in the container.

The diaphragm 36 (or the 56, 76, 96) is configured to minimize splashing of the preservative liquid L from the container 24. After the shaft 104 is snapped along the break line 110, the cover 26 (FIG. 6) is applied to the container 24 and the collected cells are preserved in the preservative liquid L and later randomized, enriched, pipetted, stained on a slide, and analyzed for cytology screening and categorization.

Figure 8:
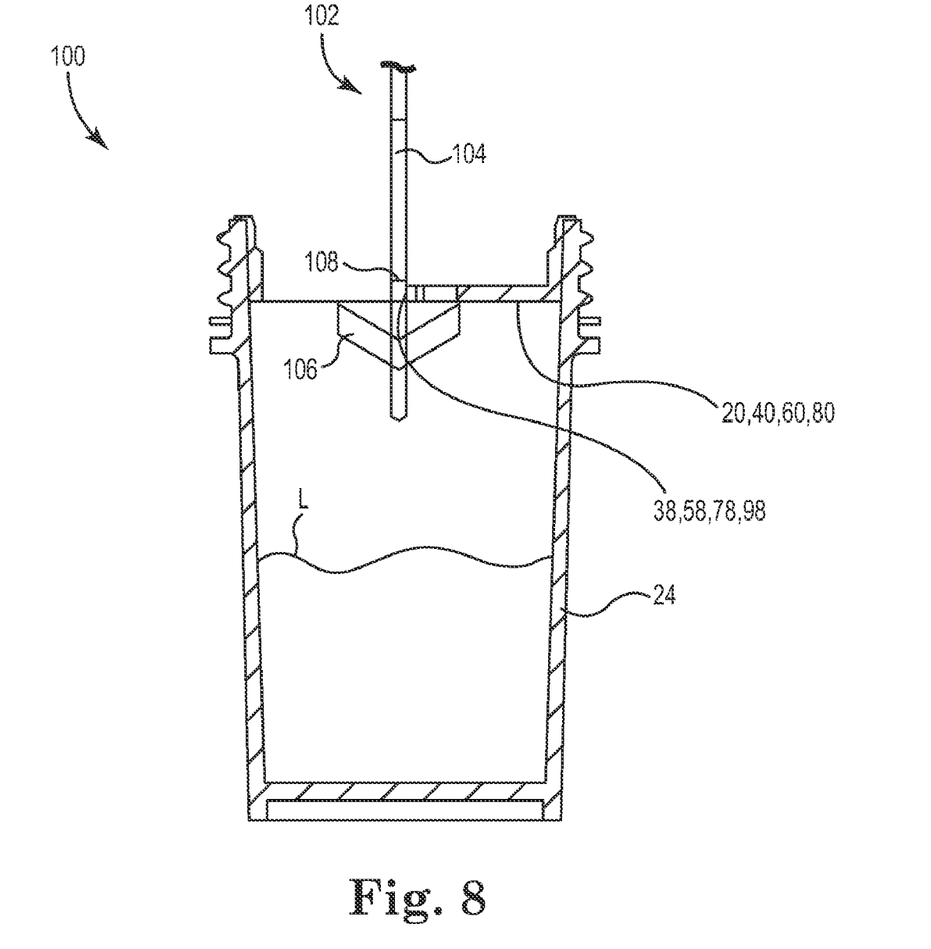
FIG. 8 is a schematic cross-sectional view of the sampling device of FIG. 6 engaged with the cap according to one embodiment.

FIG. 8 is a schematic cross-sectional view of the sampling device 102 engaged with the cap 20 according to one embodiment. The cell sampler 106 has been inserted through A1 and the shaft 104 has traversed the channel C until the sampler 106 is engaged with the smaller area A2 under the diaphragm. In this example, sampling device 102 has a broom-type detachable cell sampler 106. A portion of the cell sampler 106 is engaged with the boundary 38 (or the boundary 58, 78, 98) of the respective one of the caps 20, 40, 60, 80. An upward force applied to the shaft 104 detaches the cell sampler 106 from the shaft 104 along the detach line 108, resulting in the cell sampler 106 dropping into the preservation liquid L. Thereafter, the cover 26 (FIG. 6) is applied to the container 24 and the collected cells are preserved in the preservative liquid L and later randomized, enriched, pipetted, stained on a slide, and analyzed for cytology screening and categorization.

It is to be understood that the various embodiment of the diaphragms and boundaries described above are modified to include angled (or sharp) boundaries suited for shearing the shaft of the sampler. The diaphragms need not be horizontal and can include curvature into or out of the container.

The embodiments described in FIGS. 7 and 8 include a central boundary edge 38, 58, 78, 98 for detaching the cell sampler 106 from the sampling device 102. The central location of the boundary 38, 58, 78, 98 minimizes the risk of tipping the container 24 when detaching the sampler 106. The configuration illustrated in FIG. 7 provides a fulcrum edge at location 38 that is effective in separating sampler 106 from the shaft 104 while minimizing splashing of the preservation liquid L. The configuration illustrated in FIG. 8 employs an upward force in separating sampler 106 from the shaft 104, which minimizes tipping of the container 24 and splashing of the preservation liquid L.

Although specific embodiments have been illustrated and described herein, it will be appreciated by those of ordinary skill in the art that a variety of alternate and/or equivalent implementations may be substituted for the specific embodiments shown and described without departing from the scope of the present invention. This application is intended to cover any adaptations or variations of caps for gynecological sampling jars. Therefore, it is intended that this invention be limited only by the claims and the equivalents thereof.

What is claimed is:

1. A cap for a container configured to retain a gynecological sample collected with a sampling device having a distally located sampler coupled to a shaft, the cap comprising:
    a peripheral wall extending between a base and a flange opposite the base, the flange projecting outward from the peripheral wall and configured to seat against a rim of the container;
    a diaphragm extending from the base of the peripheral wall, the diaphragm defining a first open area communicating with a second open area that is smaller than the first open area and comprising a boundary spaced from the peripheral wall that is configured to detach the distally located sampler from the sampling device; and
    wherein the boundary comprises a channel area positioned between the first open area and the second open area and communicating with the first open area and the second open area, and wherein the channel area is defined by a lateral dimension that is narrower than a lateral dimension of the first open area and a lateral dimension of the second open area, wherein the lateral dimension of the channel area represents a width of the channel area and is parallel to the lateral dimensions of the first and second open areas.

2. The cap of claim 1, wherein the channel area is disposed at a middle of the diaphragm such that the boundary comprises a central boundary of the diaphragm.

3. The cap of claim 1, wherein the channel area defines a constriction that is configured to detach the distally located sampler from the sampling device.

4. The cap of claim 1, wherein the second open area is rectangular in shape and the boundary comprises a first corner on a first side of the channel area and a second corner separated from the first corner on an opposing second side of the channel area, the first corner intersecting with a first channel edge of the channel area and the second corner intersecting with a second channel edge of the channel area.

5. The cap of claim 4, wherein the first corner and the second corner each comprise a right angle corner.

6. The cap of claim 1, wherein the boundary comprises a fulcrum edge configured to apply a mechanical advantage to the shaft and break the shaft.

7. The cap of claim 1, wherein the diaphragm comprises a rigid material.

8. The cap of claim 1, wherein the diaphragm comprises a covered area configured to minimize splashing of liquid from the container, the covered area equal to a sum of the first open area and the second open area.

9. The cap of claim 1, wherein the peripheral wall is sized to be inserted into an inside diameter of the container.

10. The cap of claim 1, wherein the peripheral wall is sized to form a liquid seal against an inside diameter of the container.

11. A gynecological sampling system comprising:
    a sampling device comprising a shaft and a cell sampler coupled to a distal end of the shaft, wherein the cell sampler is detachable from the shaft;
    a container and a cover configured to retain preservative liquid; and
    a cap configured to be inserted between the container and the cover, the cap comprising:
        a peripheral wall extending between a base and a flange opposite the base, the flange projecting beyond the peripheral wall and configured to seat against a rim of a top opening of the container,
        a diaphragm extending from the base of the peripheral wall, the diaphragm defining a first open area communicating with a second open area, wherein the diaphragm defines a channel area positioned between the first open area and the second open area and communicating with the first open area and the second open area, the cell sampler is insertable into the first open area, and the channel area is smaller than first open area and the cell sampler;
    wherein the diaphragm is configured to minimize splashing of the preservative liquid from the container, wherein the channel area defines a constriction that is configured to detach the cell sampler from the shaft of the sampling device, and wherein the channel area is defined by a lateral dimension that is narrower than a lateral dimension of the first open area and a lateral dimension of the second open area, wherein the lateral dimension of the channel area represents a width of the channel area and is parallel to the lateral dimensions of the first and second open areas.

12. The system of claim 11, wherein the diaphragm comprises a fulcrum edge configured to apply a mechanical advantage to break the shaft when the sampling device is engaged with the cap and the container.

13. The system of claim 12, wherein a perimeter of the channel area includes the fulcrum edge.

14. The system of claim 12, wherein the perimeter of the first open area comprises a base edge adjacent to the peripheral wall, the base edge comprising the fulcrum edge.

15. The system of claim 14, wherein the perimeter of the second open area is rectangular in shape and the base edge is linear.

* * * * *